United States Patent [19]
Roos

[11] Patent Number: 4,898,089
[45] Date of Patent: Feb. 6, 1990

[54] LAMINAR FLOW WORK TABLE WITH CONTROLLABLE VENTILATION OF A WORK SURFACE

[76] Inventor: George B. Roos, 22 Berkshire Dr., Berkeley Heights, N.J. 07922

[21] Appl. No.: 187,216

[22] Filed: Apr. 28, 1988

[51] Int. Cl.[4] ............................................. B05B 15/12
[52] U.S. Cl. ............................. 98/115.1; 55/DIG. 18
[58] Field of Search .......................... 98/115.1, 115.3; 422/104; 55/DIG. 18

[56] References Cited

U.S. PATENT DOCUMENTS

| | | |
|---|---|---|
| 238,038 | 2/1881 | Frazee . |
| 401,554 | 4/1889 | Green . |
| 445,327 | 1/1891 | De Barr . |
| 549,675 | 11/1895 | Maxwell et al. . |
| 1,039,708 | 10/1912 | Denquer . |
| 1,130,890 | 3/1915 | Clayton . |
| 1,793,489 | 2/1931 | Johnson et al. . |
| 1,960,392 | 5/1934 | Ormsbee . |
| 2,110,991 | 3/1938 | Gabrielsen ........................ 98/115.1 |
| 2,467,505 | 4/1949 | Sidell ............................. 98/115.1 X |
| 3,701,514 | 10/1972 | Walters et al. ................. 98/115.1 X |
| 3,715,972 | 2/1973 | Kelso et al. ....................... 98/115.1 |
| 3,756,217 | 9/1973 | Field ............................... 98/115.1 X |
| 3,874,754 | 4/1975 | Saunders et al. .............. 98/115.3 X |
| 3,894,480 | 7/1975 | Birdsall et al. ...................... 98/115.1 |
| 3,926,597 | 12/1975 | Landy ............................ 98/115.3 X |
| 4,098,174 | 7/1978 | Landy ............................... 98/115.3 |
| 4,100,847 | 7/1978 | Norton ............................. 98/115.3 |
| 4,248,162 | 2/1981 | Skeist ............................. 98/115.1 X |
| 4,249,463 | 2/1981 | Hornby ............................. 98/115.3 |
| 4,297,940 | 11/1981 | Hainline ............................. 98/33.1 |
| 4,600,557 | 7/1986 | Spitz ....................................... 422/4 |
| 4,647,295 | 3/1987 | Christ ...................................... 55/97 |
| 4,666,478 | 5/1987 | Boissinot et al. ...................... 55/279 |

FOREIGN PATENT DOCUMENTS

| | | | |
|---|---|---|---|
| 61230 | 5/1948 | Netherlands ........................ 98/115.1 |
| 867003 | 5/1961 | United Kingdom ............... 98/115.1 |
| 2068107 | 8/1981 | United Kingdom ............... 98/115.1 |
| 2158226 | 11/1985 | United Kingdom ............... 98/115.1 |

Primary Examiner—Harold Joyce
Attorney, Agent, or Firm—Indyk, Pojunas & Brady

[57] ABSTRACT

A laminar flow work table has a perforated work surface positioned and supported a predetermined distance above a floor surface. The perforated work surface is divided into sections. Each section communicates with a separate duct communicating with the perforations in its respective section and extending to a common exhaust manifold connected with a return duct in a ventilation system where the table is situated. Each section of the work surface is ventilated by drawing fluid through the perforations into the ductwork and out to the return duct through the common manifold. Each duct has a baffle which controls the flow of fluid in its respective duct which permits the ventilation in various parts of the work table to be balanced. This arrangement permits the work table to be adequately and uniformly ventilated so that noxious fluids may be effectively removed from the vicinity of the work table so that a worker is not exposed to dangerous, unpleasant, or unhealthful conditions. This arrangement is particularly useful as a work table to be used in performing autopsies and other like procedures which produce dangerous or unpleasant contamination of the work environment.

18 Claims, 4 Drawing Sheets

LAMINAR FLOW WORK TABLE WITH CONTROLLABLE VENTILATION OF A WORK SURFACE

FIELD OF THE INVENTION

This invention relates to ventilated work tables. More particularly, it relates to ventilated work tables with controllable amounts of ventilation.

BACKGROUND OF THE INVENTION

Some industrial, scientific, medical, and commercial activities involve workers performing tasks at work tables which result in the production of any of a number of noxious or unpleasant substances to which those workers might be exposed as they carry out their activities. Some examples of such activities include the performance of autopsies, dissections, and embalming procedures, the fabrication of electronic circuitry, the manipulation of toxic substances such as hazardous chemicals or biological material, or any activity which might produce airborne contamination.

In the past, efforts have been made to ventilate the work areas where these kinds of activities are carried out. In some instances, specially designed ventilation systems have been constructed for the room where the activity of concern is being carried out. In other instances, individual work tables or work stations in the room have been ventilated in some manner in an attempt to further protect workers from being exposed to undesirable contamination. In none of these cases has a system been devised which permits a sufficiently versatile, efficient, or controllable ventilation system for a work area. In addition, many of such ventilation systems have been cumbersome in that they are constructed so that they take up too much space and restrict a worker's activities, for example, as in laboratory fume hoods which allow access only from the front. In some cases, those fume hoods further restrict access in the front by the use of windows or sashes.

For example, U.S. Pat. No. 3,701,514 refers to a table used in cutting steel plate. The table has a series of channels extending under a grating which supports a metal workpiece undergoing a cutting operation. There is a hinged cover for each of the channels which opens when a plasma cutting torch is situated over its respective channel or over a channel adjacent to its respective channel. When a hinged cover opens, its channel is connected to an exhaust manifold so that the channel is exhausted of the fumes and smoke produced by the cutting operation. At other times, each of the hinged covers seals its respective channel from the manifold and the channel is not exhausted. Plainly, this type of an arrangement permits the ventilation of only a small part of the work surface at any one time. Moreover, it does not permit the ventilation to be controlled in any meaningful manner, either over a small area encompassed by a single channel or over a larger area encompassed by more than one channel.

U.S. Pat. No. 3,715,972 deals with a laminar flow clean work station composed of interchangeable work modules containing items such as sinks, hot plates and the like, each of which is connected to a common exhaust plenum. Each of the modules has a separate exhaust damper suitable for the particular exhaust requirement of each module. There is no suggestion about how to provide proper and controllable ventilation of a large area work surface.

U.S. Pat. No. 3,894,480 refers to a laboratory bench having an exhaust plenum with an inlet vent above a table top. The exhaust plenum is divided into a number of exhaust chambers, each containing an intake mouth of an exhaust conduit. Dampeners in a chimney connected to the exhaust conduits control the intake flow from the chambers of the exhaust plenum. This arrangement does not provide sufficient or controllable ventilation over the entire surface of a work table.

U.S. Pat. No. 4,100,847 deals with a laminar airflow cabinet having an adjustable damper for changing the airflow pattern in the cabinet to supposedly meet specialized ventilation requirements when working with potentially hazardous biological substances. A knee well is provided in the front of the cabinet. U.S. Pat. Nos. 3,926,597 and 4,098,174 also refer to knee spaces in laminar flow cabinets.

None of the patents described above deal with a device which is able to effectively and controllably ventilate the entire surface of a work table. None of them show an apparatus which provides adequate ventilation while at the same time providing convenient and comfortable operator access to three or four sides of a work table. They are indicative of a long felt and unfulfilled need for such a device and of many attempts to satisfy that need without success.

The invention of this application addresses this need for a superior ventilated work table not provided by the prior efforts of others.

Accordingly, it is an object of the invention to provide a work table which is adequately ventilated to prevent workers from being exposed to noxious and harmful substances when working at the table.

It is an additional object of the invention to provide a work table in which the adequate ventilation is provided over the entire work surface of the table.

It is another object of the invention to provide a work table in which the amount of ventilation is controllable over the entire surface of the table.

It is also an object to provide a ventilated work table which does not interfere with the activities of workers using the work table.

It is also an object of the invention to provide a ventilated work table which is capable of effectively and controllably evacuating both wet and dry substances, including gases containing liquid droplets and solid particulate matter, from the surface of the work table.

Other objects and advantages are either specifically described elsewhere in this application or are apparent from that description.

SUMMARY OF THE INVENTION

In accordance with the objects of the invention identified above, the invention of this application comprises a work table having a generally horizontal perforated work surface located at a predetermined distance from a floor surface. A first duct means communicates with some of the perforations in the work surface and is connected to a common exhaust manifold. A second duct means communicates with others of the perforations in the work surface and is also connected to the common manifold. In one example of the invention described in detail in this application, there is a third duct means which communicates with yet another set of perforations in the work surface. There is a controllable baffle means in each of the duct means to regulate the flow of fluid through the duct means. The baffle means may be set to provide predetermined fluid flows through the perforations and the duct means, for example, the baffle means may be set so that there are equal flow rates in the duct means.

Additional details of a specific example of the invention are set forth below. The full scope of the invention is set forth in the claims after the description of the specific example.

DETAILED DESCRIPTION OF A SPECIFIC EXAMPLE OF THE INVENTION

Figure 1:
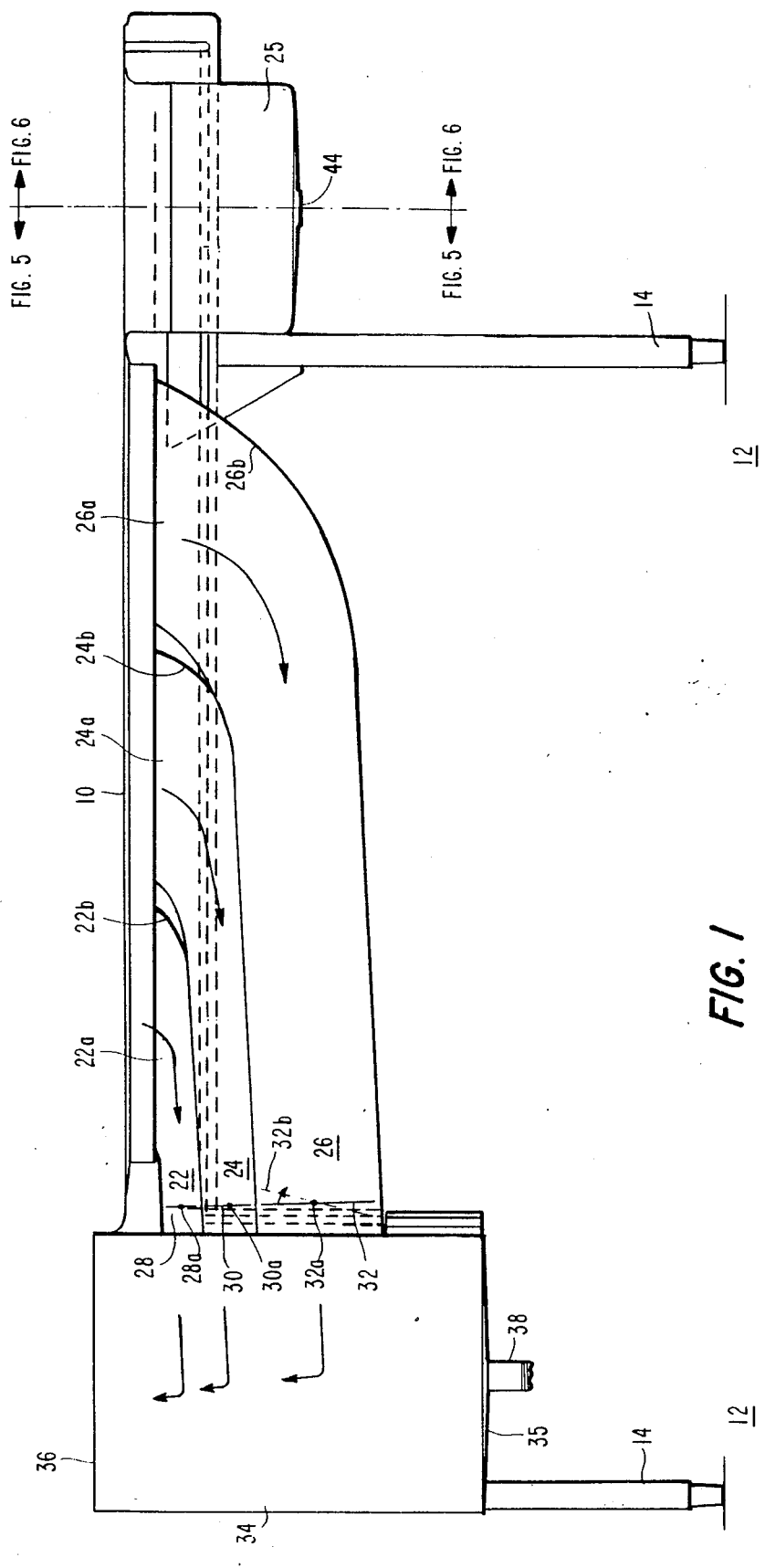
FIG. 1 is a front cross sectional view of a work table in accordance with a specific example of the invention of this application.
Figure 2:
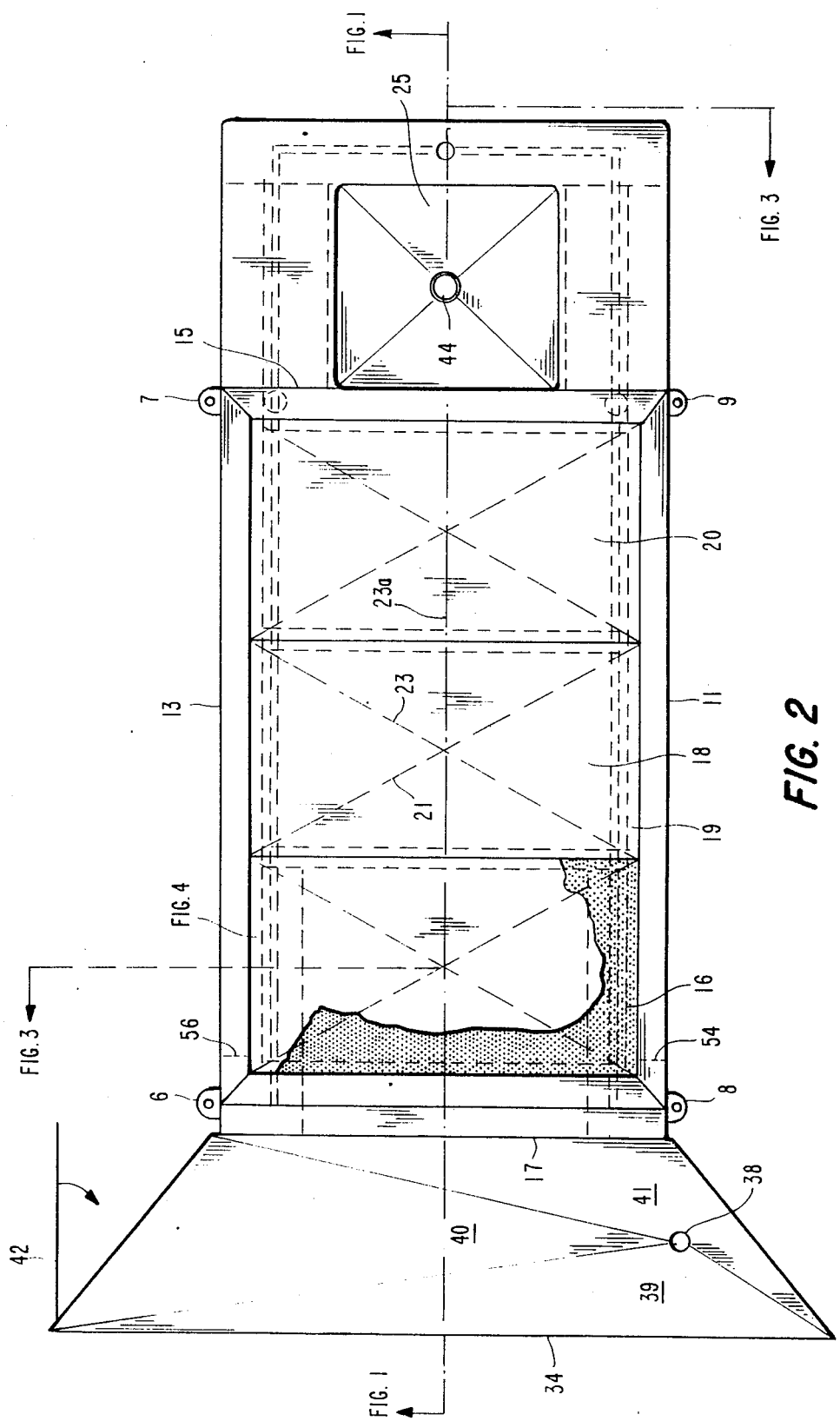
FIG. 2 is a top view of the work table of FIG. 1, parts of which are shown broken away to illustrate certain aspects of the work table.
Figure 3:
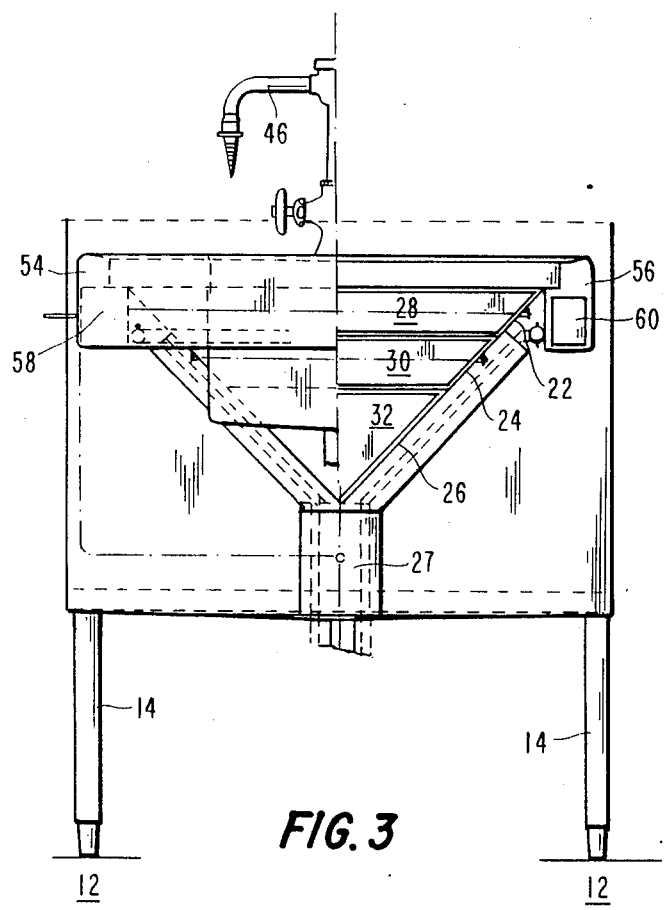
FIG. 3 is a partial sectional side view of the work table of FIG. 1.
Figure 4:
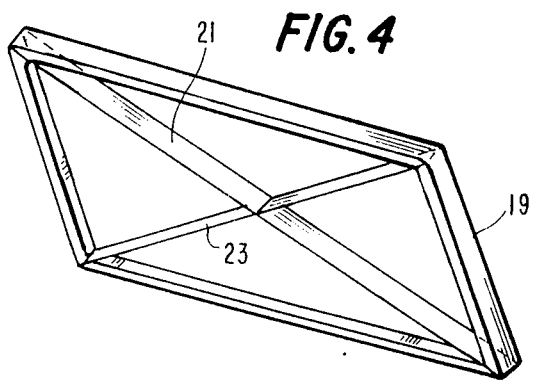
FIG. 4 is a perspective view of the removable braced trays shown in FIG. 1.

FIGS. 1-3 show an example of a work table in accordance with the invention of this application comprising a generally horizontal work surface 10 supported at a predetermined distance above a floor surface 12 by four legs 14. As shown most clearly in FIG. 2, the work surface 10 is generally rectangular and comprises a front edge 11, a back edge 13, and two side edges 15 and 17. The table is provided with four hand hose brackets 6, 7, 8, and 9 which permit the work environment to be conveniently flushed with water from hoses connected to a water supply and inserted into eyelets in the hose brackets 6-9. The work surface is divided into sections 16, 18, and 20. Each section 16, 18, and 20 comprises a generally rectangular perforated sheet, which may be made of metal, supported on and attached to a removable tray, one of which is shown in FIG. 4 and is labeled in that Figure with a reference numeral 19. As illustrated in FIG. 4, each tray is reinforced by a pair of diagonally extending cross braces 21 and 23. Each tray and its attached perforated sheet may be removed from the table for cleaning or to change the sheet to one that has desired characteristics such as different perforation sizes to achieve a different desired performance.

The dimensions of each of the sections 16, 18, and 20 may be, for example, about 1.25 feet by about 2.33 feet. Each of the sections 16, 18, and 20 comprises a sheet which has an array of closely spaced perforations to permit the passage of fluid through the sheet. By way of example, the perforations may be circular holes about one eighth inch in diameter spaced so that they have a density of about 35 holes per square inch. The holes may be in rows, with adjacent rows being staggered with respect to each other.

As shown most clearly in FIG. 1, the perforated sheets forming the work surface 10 cover the inlets 22a, 24a, and 26a to three exhaust ducts 22, 24, and 26, respectively. Exhaust duct 22 is directly beneath the work surface 10, exhaust duct 24 is directly beneath exhaust duct 22, and exhaust duct 26 is directly beneath exhaust duct 24. Those exhaust ducts extend parallel to the front and back edges 11 and 13 along the longitudinal axis 23 of the work table.

As shown in FIGS. 1 and 3, as the exhaust ducts get closer to the floor, they are tapered toward the center part of the table to provide knee space around the edges of the table for the comfort and convenience of workers seated at the table. For example, the side walls of the ducts may be oriented at about a 45 degree angle with respect to the vertical, as shown in FIG. 3. Sufficient knee space for the front edge 11 and the rear edge 13 is accomplished in this example of the invention by providing the exhaust ducts 22 and 24 with a trapezoidal cross sections and providing the exhaust duct 26 with a triangular cross section. Sufficient knee space is provided for the edge 15 by the curving of the ducts away from that edge as indicated by reference numerals 22b, 24b, and 26b in FIG. 1. A narrow post 27 shown in FIG. 3, or even a relatively thin wall member extending along the longitudinal axis 23 from the bottom of the ducts to the floor, may be provided to support the ducts and the center of the work table.

Each of the ducts contains a baffle for controlling or regulating the flow of fluid through the ducts. The baffle for each of the ducts is continuously adjustable between two extreme positions defining minimum and maximum flow conditions in each duct so that the flow of fluid through each of the ducts is adjustable to all flow conditions between the minimum and maximum flow conditions as a continuous function of the position of the baffle. In the example of the invention shown in the Figures, the baffle in the duct 22 takes the form of a butterfly valve 28 rotatable about a pivot point 28a which thus produces a variable cross sectional area restriction in the duct 22 to control the magnitude of the fluid flow in the duct. Similarly, duct 24 contains a butterfly valve 30 rotatable about a pivot point 30a and duct 26 contains a butterfly valve 32 rotatable about a pivot point 32a to likewise control the fluid flow in those ducts. Phantom line 32b in FIG. 1 illustrates the rotation of valve 32 and the gradual opening of the duct 26 as the valve is rotated from its position permitting minimum flow through the duct 26, as indicated by the solid representation of the valve at reference numeral 32, to its position permitting maximum flow, when the valve is generally parallel to the upper and lower walls of the duct 26. Valves 28 and 30 operate similarly.

As shown in FIG. 3, the valves have cross sectional configurations closely resembling the cross sectional configurations of the ducts in which they are located. Specifically, valves 28 and 30 have a trapezoidal configuration and valve 32 has a triangular configuration. There may be about one half inch of space between the perimeter of the valves and the walls of the ducts. As the valves are rotated from the positions in which they are shown in FIG. 3, they present a variable cross sectional area transverse to the flow of fluid in their respective ducts and thus vary the amount by which they block or restrict fluid flow in those ducts.

The cross sectional area of each of the ducts 22, 24, and 26 transverse to the flow of fluid is sized such that a desired fluid flow may be maintained through the ducts and an adequate ventilation of the work surface is achieved. The cross sectional areas of the ducts at the inlets 22a, 24a, and 26a are approximately the same as that of sections 16, 18, and 20 of the work surface. The cross sectional areas may gradually decrease to areas somewhat larger than the cross sectional areas of the valves, as shown in FIG. 3, for example, there may be one half inch space all the way around the baffle in each duct. By way of example, over as much of the lengths of the ducts as possible, the height of duct 22 may be about 2 and ⅜ inches, the height of duct 24 may be about 3 and ⅛ inches, and the height of duct 26 may be about 7 and ½ inches from the base to the apex of the triangle defined by the cross section of the duct 26. The cross sectional areas transverse to the flow of fluid in the ducts preferably are equal over as much of the lengths of the ducts as is possible or practical.

The cross sections have the same shape as the sections 16, 18, and 20 at the inlets to the ducts. As close to the inlets as is practical, the configuration of the cross sections of the ducts transverse to fluid flow is gradually changed to the trapezoidal cross sections and the triangular cross section shown in FIG. 3. In a preferred arrangement, as indicated above the cross sectional areas of the ducts transverse to the flow of fluid in the ducts are equal for all three ducts over as much of the lengths of the ducts as is possible or practical. Also in that preferred arrangement, the baffles in the ducts are set so that the fluid flows through the ducts are balanced or substantially equal so that the ventilation is uniform over the entire area of the work surface.

The outlets of the ducts 22, 24, and 26 are connected to a common exhaust manifold 34 by means of any well known means for connecting ducting to a manifold so that fluid does not leak through the connection. The manifold 34 may be similarly connected at the top 36 to a return duct in a ventilation system, such as an air conditioning system or air purification system, provided for the room in which the work table is being used. The manifold may also be connected to a ventilation system dedicated solely to the work table.

The floor 35 of the common exhaust manifold 34 contains a drain 38 for the draining of liquid and solid components in the fluid streams from the ducts 22, 24, and 26. As shown in FIG. 2, the floor of the common exhaust manifold 34 has sections 39, 40, and 41 which slope toward the drain to assist in the drainage of those components. A hinged door 42 may be provided in one or more of the sides of the common exhaust manifold to provide access to the interior of the manifold.

In operation, through the action of whatever motive means is used in the ventilation system to create motion of fluid through the system, a laminar flow of air is drawn vertically down through the perforated sections 16, 18, and 20, through the ducts 22, 24, and 26, through the outlets of the ducts 22, 24, and 26, through the baffles 28, 30, and 32, and into the common exhaust manifold 34, where the flow of air becomes reduced in speed, because of the fact that the volume of the manifold 34 is much larger than that of the ducts, and where the flow of air makes a sharp turn upwardly to the top 36 of the manifold 34. The flow paths taken by the air are illustrated with arrows in FIG. 1. Because of the reduction in speed and the sharp upward turn of the fluid coming from the ducts into the common exhaust manifold, the liquid and solid matter that may be present in the fluid streams tends to drop out of the fluid streams and drain out of the manifold through the drain 38.

In another example of the invention, in a situation where the return duct for a ventilation system is located beneath the table, for example, in the floor, the fluid streams from the ducts may be directed downwardly toward the floor underneath the table. The common manifold is again connected to the return duct and may be situated either above the floor level under the table or it may be located under the floor. In this situation, the ducting may be directed and the manifold may be located so that the work table may be used as an island work table approachable from all sides by those working at the table.

Figure 5:
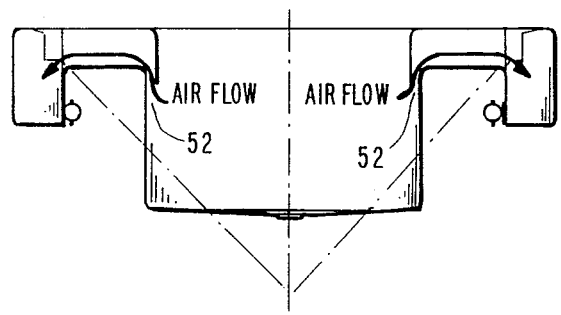
FIGS. 5 and 6 are sectional views of the sink shown in FIG. 1.
Figure 6:
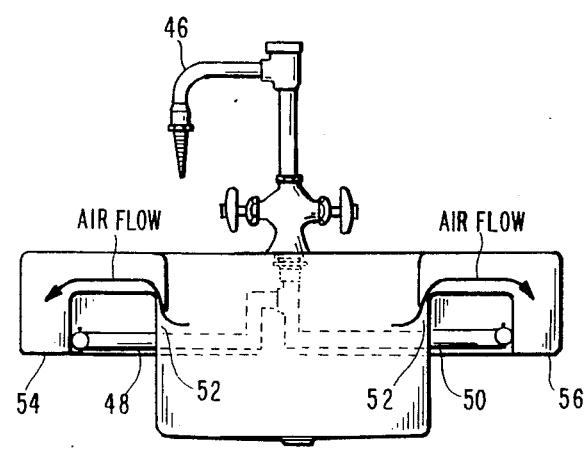

In the example of the invention shown in the drawings of this application, the ventilated work table may have a sink 25 attached to the edge 15 of the table. The sink is provided with a conventional drain 44 and a conventional hot and cold water faucet 46 supplied with water from conventional plumbing, such as copper tubing 48 and 50. The sink is provided with a ventilation slot 52 around its periphery. As shown by the "airflow" arrows in FIGS. 5 and 6, air is drawn into a pair of sink ducts 54 and 56 running along the front edge 11 and the rear edge 13 of the work table. The sink ducts 54 and 56 are connected to the common exhaust manifold 34. The sink duct 54 is provided with a baffle in the form of a butterfly valve 58 and the sink duct 56 is provided with another baffle in the form of a butterfly valve 60 to control the flow of fluid in the sink ducts in a manner similar to that of the control of fluid flow in the ducts 22, 24, and 26 by the butterfly valves 28, 30, and 32.

The work table in accordance with the invention of this application may be connected to a suitable ventilation system and the valves in the work surface ducts may be set so that a total fluid flow drawn by the table is about 2200–2500 cubic feet per minute evenly distributed across a work surface having a large area. The velocity of the fluid being drawn into the table may be about 70–100 feet per minute at a point about one foot above the work surface of the table. The valves for the ventilation system in the sink may be set so that fluid flows through the sink ventilation system at about 50–70 feet per minute.

In light of all of the foregoing description, a work table in accordance with the invention of this application is able to be ventilated more effectively than any prior work table and thus this work table provides a safer and more comfortable work environment because all noxious and dangerous substances, both wet and dry, are effectively and uniformly removed from the work table environment, even when the work table has a large surface area. To provide additional amounts of safety in some environments, an air filtration device or a duct incinerator device may be provided in the fluid flow paths in a work table in accordance with this invention, so that no contaminated air is exhausted in a building or into the atmosphere.

An additional advantage of a work table in accordance with the invention of this application is that any solid object placed on the perforated work surface is subject to an increased fluid velocity at the edges of the object, which improves the removal of unwanted contamination in the vicinity of the object.

I claim:

1. A substantially laminar flow work table, comprising:
   a generally horizontal perforated work surface supported at a predetermined distance above a floor surface;
   a first duct means situated below the perforated work surface and communicating with a predetermined first portion of the perforated work surface for permitting a fluid flow to be drawn through the first duct means and through the perforations in the predetermined first portion of the work surface, the first duct means having a predetermined cross sectional configuration and area transverse to the flow of fluid in the first duct means;

a first controllable baffle means situated in the first duct means for controlling the flow of fluid through the first duct means and the perforations in the predetermined first portion of the work surface, the first baffle means being continuously adjustable between two extreme positions defining minimum and maximum flow conditions, so that the flow of fluid through the first duct means and the perforations in the predetermined first portion of the work surface is adjustable to all flow conditions between the minimum and maximum flow conditions as a continuous function of the position of the first baffle means;

a second duct means situated below the first duct means and communicating with a predetermined second portion of the perforated work surface for permitting a fluid flow to be drawn through the second duct means and through the perforations in the predetermined second portion of the work surface, the second duct means having a predetermined cross sectional configuration and area transverse to the flow of fluid in the second duct means;

a second controllable baffle means situated in the second duct means for controlling the flow of fluid through the second duct means and the perforations in the predetermined second portion of the work surface, the second baffle means being continuously adjustable between two extreme positions defining minimum and maximum flow conditions, so that the flow of fluid through the second duct means and the perforations in the predetermined second portion of the work surface is adjustable to all flow conditions between the minimum and maximum flow conditions as a continuous function of the position of the second baffle means; and a means for connecting the first and second duct means to a common exhaust manifold.

2. The apparatus of claim 1, further comprising:
a third duct means situated below the second duct means and communicating with a predetermined third portion of the perforated work surface for permitting a fluid flow to be drawn through the third duct means and through the perforations in the predetermined third portion of the work surface, the third duct means having a predetermined cross sectional configuration and area transverse to the flow of fluid in the third duct means; and a third controllable baffle means situated in the third duct means for controlling the flow of fluid through the third duct means and the perforations in the predetermined third portion of the work surface, the third baffle means being continuously adjustable between two extreme positions defining minimum and maximum flow conditions, so that the flow of fluid through the third duct means and the perforations in the predetermined third portion of the work surface is adjustable to all flow conditions between the minimum and maximum flow conditions as a continuous function of the position of the third baffle means; and a means for connecting the third duct means to the common exhaust manifold.

3. The apparatus of claim 1, in which the first and second baffle means are adjusted so that the flows of fluid through the first and second duct means have a predetermined relationship.

4. The apparatus of claim 3, in which the predetermined relationship is such that the fluid flows through the first and second duct means are substantially equal.

5. The apparatus of claim 3, in which the predetermined relationship is such that the flow of fluid through the perforations in the work surface is substantially uniform over substantially the entire area of the work surface.

6. The apparatus of claim 1, in which the predetermined cross sectional configuration of the first and second duct means is tapered to provide knee space for a worker seated at the work table.

7. The apparatus of claim 1, in which the predetermined cross sectional configuration is such that at least one of the first or second duct means has a trapezoidal cross section transverse to the flow of fluid through that duct means.

8. The apparatus of claim 1, in which the predetermined cross sectional configuration is such that at least one of the first or second duct means has a triangular cross section transverse to the flow of fluid through that duct means.

9. The apparatus of claim 1, in which the predetermined cross sectional configuration is such that the first duct means has a trapezoidal cross section transverse to the flow of fluid in the first duct means and the second duct means has a triangular cross section transverse to the flow of fluid through the second duct means.

10. The apparatus of claim 1, in which the predetermined cross sectional areas of the first and second duct means are substantially equal.

11. The apparatus of claim 1, further comprising:
a sink attached to the work surface;
one or more openings in the sink for the passage of fluid;
a sink exhaust duct communicating with the one or more openings in the sink for exhausting fluid from the vicinity of the sink by permitting a fluid flow to be drawn through the openings in the sink and through the sink exhaust duct, the sink exhaust duct extending from the vicinity of the sink along the edges of the work surface to the common exhaust manifold; and
a controllable sink exhaust baffle means in the sink exhaust duct for controlling the flow of fluid through the sink exhaust duct and the one or more openings in the sink, the sink exhaust baffle means being continuously adjustable between two extreme positions defining minimum and maximum flow conditions, so that the flow of fluid through the sink exhaust duct and the one or more openings in the sink is adjustable to all flow conditions between the minimum and maximum flow conditions as a continuous function of the position of the second baffle means.

12. The apparatus of claim 1, further comprising:
a means in the common exhaust manifold for removing from the fluid streams in the first and second duct means any solids or liquids present in the fluid streams.

13. The apparatus of claim 12, in which the means for removing solids and liquids from the fluid stream comprises:
a means for changing the direction and the speed of the fluid flowing in the first and second duct means; and
a drain in the common exhaust manifold.

14. The apparatus of claim 1, in which the baffle means in the first and second duct means comprise butterfly valves in the first and second duct means.

15. The apparatus of claim 2, in which the baffle means in the first, second, and third duct means comprise butterfly valves in the first, second, and third duct means.

16. The apparatus of claim 2, in which the cross sectional configuration of the first and second duct means is trapezoidal and the cross sectional configuration of the third duct means is triangular.

17. The apparatus of claim 2, in which the baffling means are set to balance the fluid flows through the first, second, and third portions of the perforated work surface.

18. The apparatus of claim 2, in which the predetermined cross sectional areas of the first, second, and third duct means are substantially equal.

* * * * *